United States Patent [19]

Jaimes et al.

[11] Patent Number: 5,655,905
[45] Date of Patent: Aug. 12, 1997

[54] MOBILE MULTIFUNCTIONAL DENTAL APPARATUS

[76] Inventors: Jairo Jaimes; Rolando Rodriguez, both of 137-40 45th Ave., Apt. 1A, Flushing, N.Y. 11355

[21] Appl. No.: 542,414

[22] Filed: Oct. 12, 1995

[51] Int. Cl.$^6$ ................................................. A61C 15/00
[52] U.S. Cl. ........................................... 433/77; 312/209
[58] Field of Search ............................ 433/77, 79, 108; 312/209

[56] References Cited

U.S. PATENT DOCUMENTS

| | | | |
|---|---|---|---|
| 2,308,812 | 1/1943 | Jankelson | 433/77 |
| 2,351,943 | 6/1944 | Ebbers et al. | 433/77 |
| 3,455,620 | 7/1969 | Coburn | 433/77 |
| 5,013,240 | 5/1991 | Bailey et al. | 433/77 |
| 5,211,558 | 5/1993 | Bailey et al. | 433/77 |
| 5,356,290 | 10/1994 | Strohmaier | 433/77 |

*Primary Examiner*—Cary E. O'Connor

[57] ABSTRACT

A mobile multifunctional dental apparatus comprising: a generally rectangular shaped outer casing having a front wall, a rear wall, sidewalls, a floor, an interior compartment, a hinged lid, a plurality of wheels and an electrical coupling device, the front wall including a plurality of switches and a lighted screen, a plurality of hoses each having a first end positioned through the outer casing and a second end including a handle control, each handle control including a device to permit activation and deactivation thereof; and the interior compartment being divided into a plurality of levels by at least one divider wall, a first level including a motorized suction device, a second level being positioned beneath the first level with an aperture extending through a divider wall separating the levels, the motorized suction device causing inward suction, a collecting basin for retaining fluid being positioned within the second level, a limit switch including a stopper plug and a floatation device positioned within the basin.

6 Claims, 3 Drawing Sheets

1

MOBILE MULTIFUNCTIONAL DENTAL APPARATUS

BACKGROUND OF THE INVENTION

1. Field of the Invention

The present invention relates to a mobile multifunctional dental apparatus and more particularly pertains to performing a wide variety of dental procedures by maneuvering the apparatus adjacent to a patient location.

2. Description of the Prior Art

The use of dental equipment is known in the prior art. More specifically, dental equipment heretofore devised and utilized for the purpose of performing dental procedures are known to consist basically of familiar, expected, and obvious structural configurations, notwithstanding the myriad of designs encompassed by the crowded prior art which has been developed for the fulfillment of countless objectives and requirements.

In this respect, the mobile multifunctional dental apparatus according to the present invention substantially departs from the conventional concepts and designs of the prior art, and in doing so provides an apparatus primarily developed for the purpose of performing a wide variety of dental procedures by maneuvering the apparatus adjacent to a patient location.

Therefore, it can be appreciated that there exists a continuing need for a new and improved mobile multifunctional dental apparatus which can be used for performing a wide variety of dental procedures by maneuvering the apparatus adjacent to a patient location. In this regard, the present invention substantially fulfills this need.

SUMMARY OF THE INVENTION

In view of the foregoing disadvantages inherent in the known types of dental equipment now present in the prior art, the present invention provides an improved mobile multifunctional dental apparatus. As such, the general purpose of the present invention, which will be described subsequently in greater detail, is to provide a new and improved mobile multifunctional dental apparatus and method which has all the advantages of the prior art and none of the disadvantages.

To attain this, the present invention essentially comprises a new and improved mobile multifunctional dental apparatus comprising, in combination: a generally rectangular shaped outer casing having a front wall, a rear wall, two sidewalls, a floor, a plurality of wheels, and an essentially hollow interior, each side wall having a front portion with a downwardly angled upper extent and extending beyond the front wall, the front portions including a cross bar affixed therebetween, each side wall having an upper region with a waste bin affixed thereto, one side wall having a lower region with at least one electrical outlet positioned therein, the rear wall and rear portion of the sidewalls having an upper extent with a hinged lid affixed thereto, a transition wall being positioned across the downwardly sloping front portions of the side walls between the front wall and hinged lid, the transition wall including a transparent screen, a florescent light being positioned behind the screen to permit viewing of x-rays, the transition wall having a lower region including a control panel with an incremental dial, a vacuum clock and a plurality of switches; a first hose, a second hose and a third hose, the second and third hose having a larger diameter than the first, each hose having a first end positioned through the front wall of the outer casing, the second end of each hose including a handle control, each handle control being coupled to the cross bar, the handle control of the first and second hoses including a releasably coupled J-shaped canula extending therefrom, the handle control of the third hose including a releasably coupled funnel shaped saliva receptacle extending therefrom; the interior of the outer casing being divided into upper, lower and central levels by first and second divider walls, the upper level being positioned beneath the lid and adapted to permit storage of various items therein, the central level being divided into a plurality of compartments and including a motorized suction device and a backup battery, the motorized suction device including a planar circular helix coupled to a rotating motor, an aperture being positioned through the first divider wall below the helix, in the operative orientation the helix being rotated by the motor thereby drawing air from the central level and causing a low pressure area in the central level, the low pressure area causing suction of air flow from the second end of the hoses through their respective first ends, an electrical control box being operatively coupled to the electrical outlets, backup battery, motorized suction device, and each handle control thereby permitting each individual handle to activate the suction device; the lower level including a plurality of upwardly extending cushion springs, a collecting basin having a bottom and an open top being positioned upon the springs, a screen being positioned over the basin and beneath the first end of the hoses to filter debris passing therethrough, a mercury absorbing device being positioned at the bottom of the basin; and a limit switch with an upper arm including a rubber stopper, a lower arm including a float, and a central member pivotally coupling the arms therebetween, the float being positioned in the basin and rising as the fluid level in the basin rises thereby causing the rubber stopper to become tightly positioned within the aperture in the first divider wall causing cessation of suction through the hoses; and the handle control of each hose being formed in a cylindrical configuration and including an upper surface and a lower surface, the lower surface being formed as a grooved hand grip, the upper surface including a pivotally coupled depressible lever biased by a resilient spring, each handle control including an aperture extending through its axis, the aperture including a sheet plug with a radial hole rotatably mounted therein, the plug being rotatable to an open position permitting the passage of air and fluid therethrough, or a closed position preventing the passage of air and fluid therethrough, a rod operatively coupling the lever to the plug, a pair of electrical wires having a first end extending within the handle control, a bolt extending from the lever to a point adjacent to the wires, upon depression of the lever the bolt engaging the wires thereby electrically activating the apparatus and causing the rod to urge the plug into an open position.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved mobile multifunctional dental apparatus which has all of the advantages of the prior art dental equipment and none of the disadvantages, such as the devices being heavy and difficult to move.

It is another object of the present invention to provide a new and improved mobile multifunctional dental apparatus which may be easily and efficiently manufactured and marketed.

It is further object of the present invention to provide a new and improved mobile multifunctional dental apparatus which is of durable and reliable constructions.

An even further object of the present invention is to provide a new and improved mobile multifunctional dental apparatus which is susceptible of a low cost of manufacture with regard to both materials and labor, and which accordingly is then susceptible of low prices of sale to the consuming public, thereby making such mobile multifunctional dental apparatus economically available to the buying public.

Still another object of the present invention is to performing a wide variety of dental procedures by maneuvering the apparatus adjacent to a patient location.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
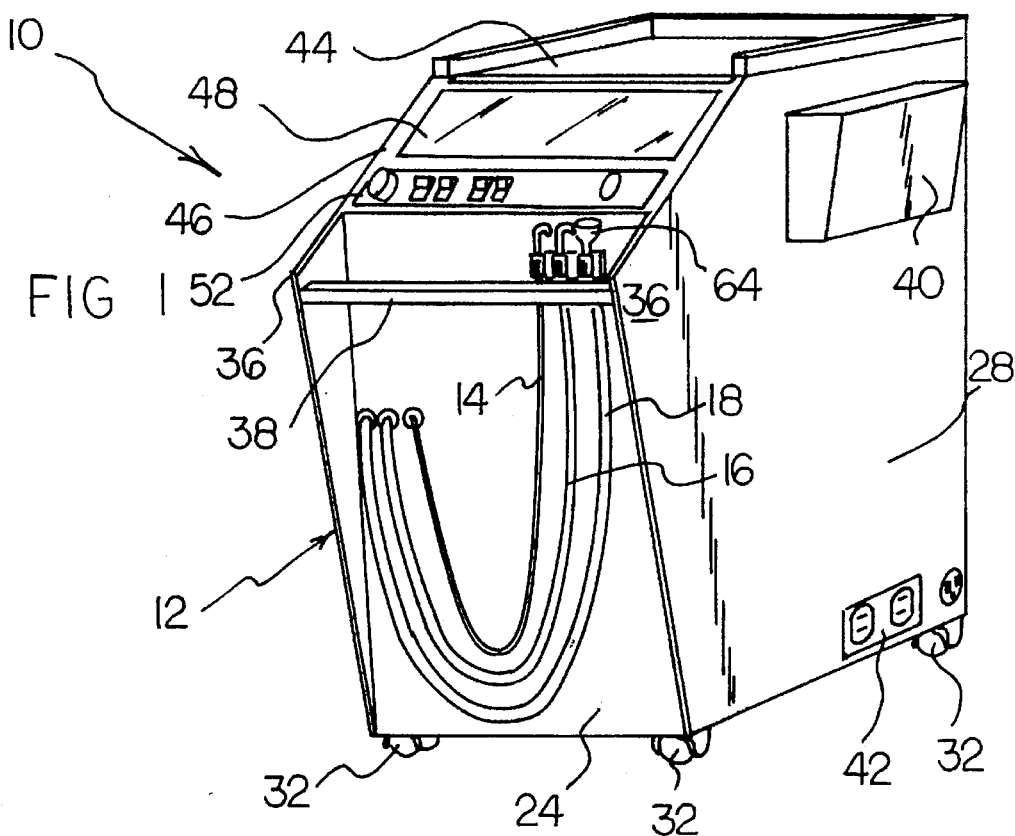
FIG. 1 is a perspective view of the preferred embodiment of the mobile multifunctional dental apparatus constructed in accordance with the principles of the present invention.

With reference now to the drawings, and in particular to FIG. 1 thereof, the preferred embodiment of the new and improved mobile multifunctional dental apparatus embodying the principles and concepts of the present invention and generally designated by the reference numeral 10 will be described.

The present invention, the mobile multifunctional dental apparatus 10 is comprised of a plurality of components. Such components in their broadest context include an outer casing 12, three hoses 14, 16, 18, a basin 20 and a limit switch 22. Such components are individually configured and correlated with respect to each other so as to attain the desired objective.

Figure 5:
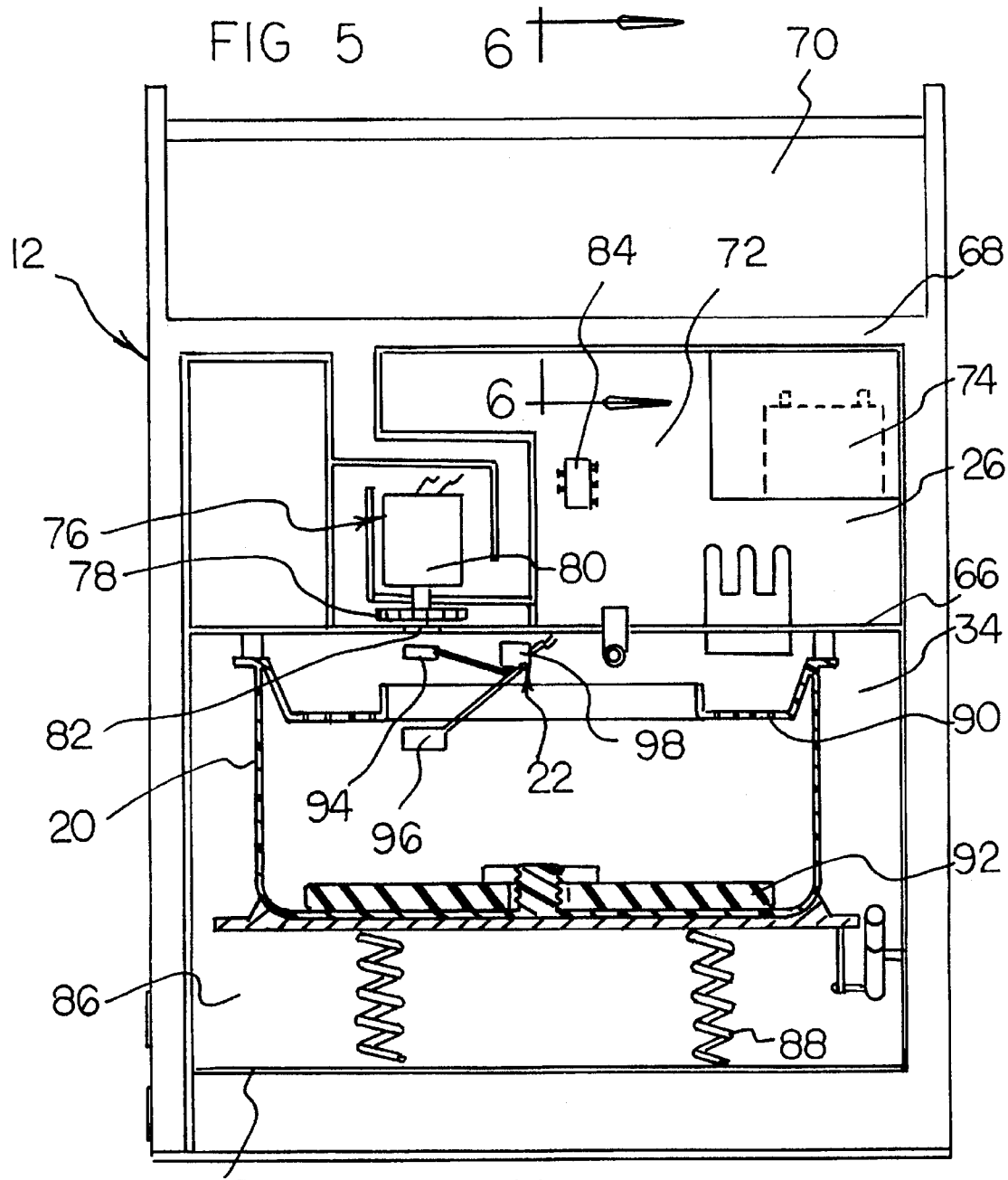
FIG. 5 is a perspective view of the interior of the mobile multifunctional dental apparatus.

More specifically, the generally rectangular shaped outer casing 12 has a front wall 24, a rear wall 26, two sidewalls 28, a floor 30, a plurality of wheels 32, and an essentially hollow interior 34. Each side wall has a front portion 36 with a downwardly angled upper extent and extends beyond the front wall. The front portions include a cross bar 38 affixed therebetween. The cross bar includes coupling devices to permit releasable coupling of the handle controls to the bar. Note FIGS. 1 and 5.

Figure 6:
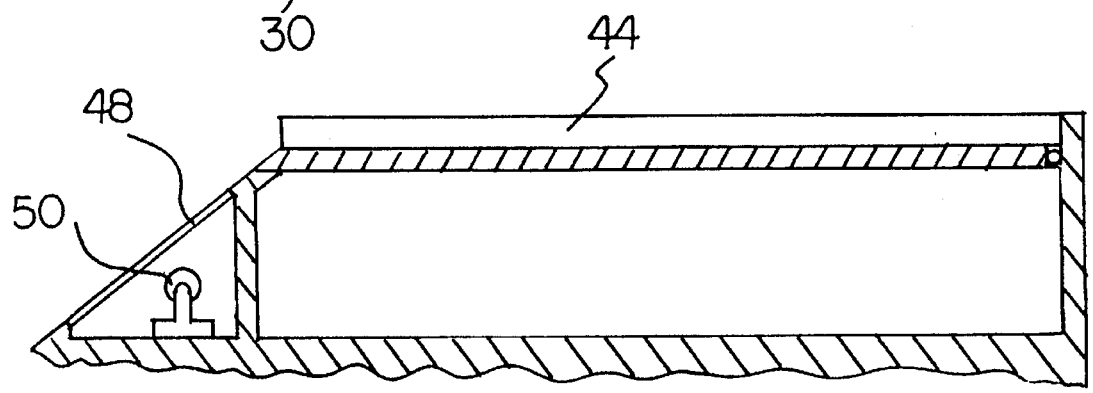
FIG. 6 is a cross sectional view of the apparatus taken along line 6—6 of FIG. 5.

Each side wall has an upper region with a waste bin 40 affixed thereto. In the preferred embodiment plastic bags are positioned within the bins. Waste materials such as needles and gauze are placed in the plastic bags and replaced after each patient is treated. One side wall has a lower region with at least one electrical outlet 42. The rear wall and rear portion of the sidewalls have an upper extent with a hinged lid 44 affixed thereto. The lid is adapted to be lifted open from the front. A large storage area is positioned beneath the lid. A wide variety of supplies and equipment may be housed in the storage area. Note FIGS. 1 and 6.

Figure 2:
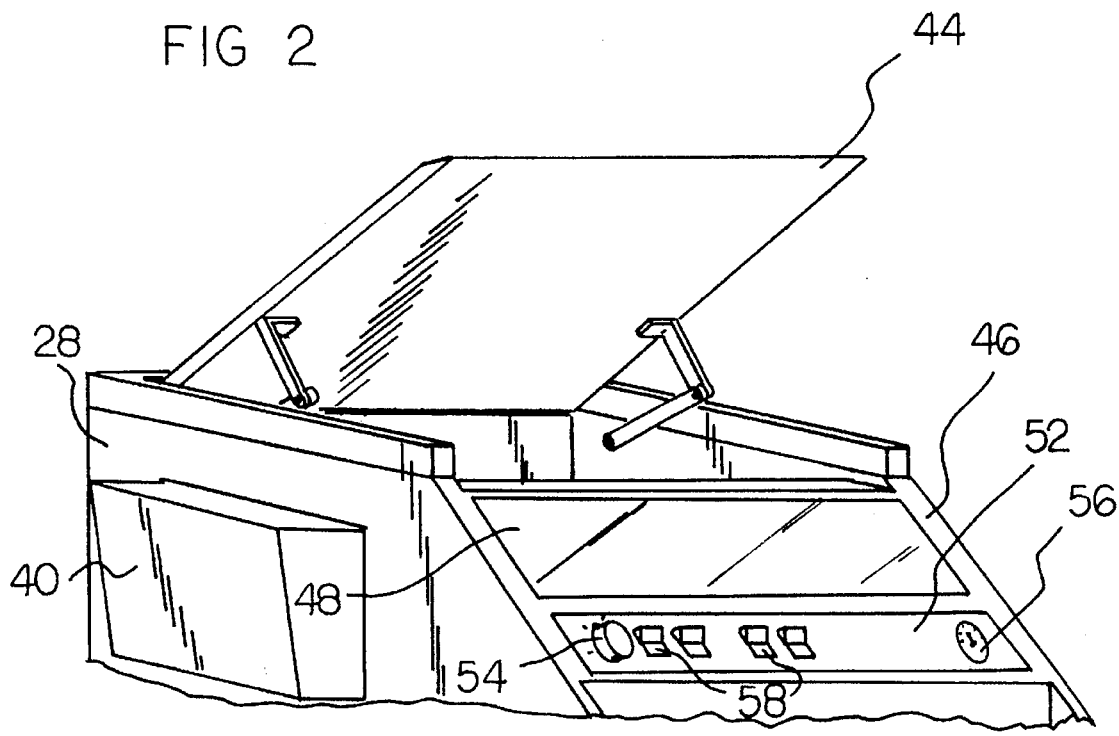
FIG. 2 is broken away perspective illustration of the apparatus with the lid positioned in an open orientation.

A transition wall 46 is positioned across the downwardly sloping front portions of the side walls between the front wall and hinged lid. The transition wall includes a transparent screen 48 and a florescent light 50. The light is positioned behind the screen to permit viewing of x-rays. The transition wall has a lower region which includes a control panel 52 with an incremental dial 54, a vacuum clock 56 and a plurality of switches 58. The incremental dial is operatively coupled to the motorized suction device and regulates the speed of the motor and magnitude of suction. The vacuum clock is operatively coupled to the motorized suction device and gauges the speed of the motor and magnitude of suction. The various switches perform the function of turning the apparatus on or off and turning the light on or off. In one embodiment of the apparatus the control panel includes a fuse to prevent overheating of the motor. In another embodiment of the apparatus the control panel includes an alarm with a red light and a sound emitting device to notify the user when the basin is filled to its capacity. Note FIGS. 1, 2 and 6.

A first hose 14, a second hose 16 and a third hose 18, are included in the apparatus. Each hose is fabricated of a flexible rubber material. The second and third hose have a larger diameter than the first. Each hose has a first end which is positioned through the front wall of the outer casing. Air, fluid and other materials suctioned through the hoses is filtered through the screen to remove particulate matter. The filtrate flows into the collecting basin and is retained there until later disposal. Note FIG. 5.

Figures 3, 4:
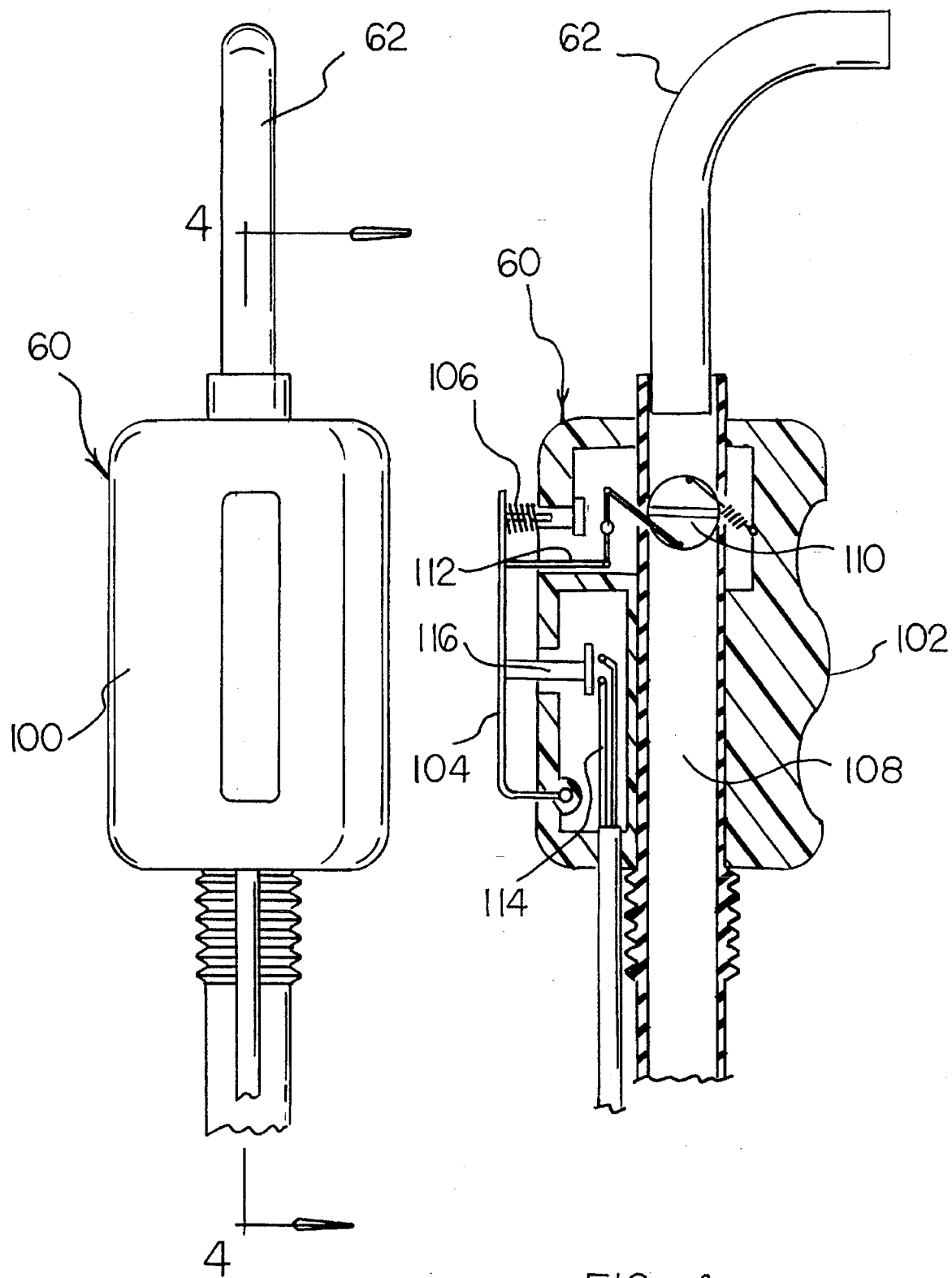
FIG. 3 is an isolated perspective illustration of the handle control component of the apparatus.
FIG. 4 is a cross sectional view of the handle control component taken along line 4—4 of FIG. 3.

The second end of each hose includes a handle control 60. This handle control will be used during specific dental procedures for the purpose of suctioning blood and sputum. Each handle control is releasably coupled to the cross bar for convenient storage. On each end of the handle control of the first and second hoses is a removable J-shaped canula 62. The cannulas enable the user to suction from difficult to reach areas of an oral cavity. On the end of the handle control of the third hose is a removable funnel-shaped saliva receptacle 64. The receptacle is designed to collect a patient's saliva upon expectorating. The cannulas and receptacle are disposable and are designed to be changed between patients to prevent disease transmission. In an Note FIGS. 1, 3, and 4.

The interior of the outer casing is divided into upper, lower and central levels by first 66 and second divider walls 68. The upper level 70 is positioned beneath the lid and adapted to permit storage of various items inside. The central level 72 is divided into a plurality of compartments and includes a backup battery 74 positioned along an inside wall of the casing. The backup battery provides power to the apparatus in case of an electrical outage. Note FIG. 5.

A motorized suction device 76 is contained in the central level of the apparatus. The motorized suction device includes a planar circular helix 78 coupled to a rotating motor 80. An aperture 82 is positioned through the first divider wall 66 below the helix. In the operative orientation, the helix is rotated by the motor thereby drawing air from the central level. This movement of air causes a low pressure area to develop in the central level. The low pressure area creates a suction flow from the second end of each hose through their respective first ends. Note FIG. 5. An electrical control box 84 is operatively coupled to the electrical outlets, backup battery, motorized suction device, and each handle control thereby permitting each individual handle to activate the suction device. Note FIG. 5.

The lower level 86 includes a plurality of upwardly extending cushion springs 88. It also contains a collecting basin 20. The basin has a bottom and an open top and is positioned upon the cushion springs. The cushion springs serve the function of absorbing vibrations during the movement of the apparatus. A screen 90 is positioned over the basin and beneath the first end of the hoses to filter debris passing through. A mercury absorbing 92 device is positioned at the bottom of the basin in order to collect mercury from amalgam and prevent water contamination. Note FIG. 5.

A limit switch 22 is affixed within the lower level between the basin and helix. The limit switch comprises an upper arm with a rubber stopper 94, a lower arm with a float 96, and a central member 98 pivotally coupling the arms in therebetween. The float is positioned in the basin and rises as the fluid level in the basin rises. This action causes the rubber stopper to become tightly positioned within the aperture in the first divider wall. This causes the cessation of suction through the hoses. Note FIG. 5.

Each handle control 60 of the apparatus is formed in a cylindrical configuration. Each handle control has an upper surface 100 and a lower surface. The lower surface is formed as a grooved hand grip 102. The upper surface includes a pivotally coupled depressible lever 104 biased by a resilient spring 106. Each handle control includes an aperture extending through its axis 108. The aperture includes a sheet plug 110 with a radial hole rotatably mounted therein. The plug is rotatable to an open position permitting the passage of air and fluid through. The plug also permits rotation into a closed position preventing the passage of air and fluid. Note FIGS. 3 and 4. A rod 112 operatively couples the lever to the plug. A pair of electrical wires 114 has a first end, which extends within the handle control. A bolt 116 extends from the lever to a point adjacent to the wires. Upon depression of the lever, the bolt engages the wires thereby electrically activating the apparatus. This causes the rod to urge the plug into an open position. Note FIGS. 3 and 4.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A mobile multi-functional dental apparatus comprising:

A) a generally rectangular shaped outer casing having a front wall, a rear wall, two sidewalls, a floor, a plurality of wheels, and an essentially hollow interior, the two side walls each having a front portion with a downwardly angled upper extent and extending beyond the front wall, the front portions including a cross bar affixed therebetween, the two side walls each having a lower region with at least one electrical outlet positioned therein, the rear wall and a rear portion of the side walls having an upper extent with a hinged lid affixed thereto, a transition wall positioned across the downwardly sloping front portions of the side walls between the front wall and hinged lid, the transition wall including a transparent screen, a florescent light positioned behind the screen to permit viewing of X-rays, the transition wall having a lower region including a control panel with an incremental dial, a vacuum clock and a plurality of switches;

B) a first hose, a second hose, and a third hose, the second and third hose each having a larger diameter than the first, each hose having a first end positioned through the front wall of the outer casing, each hose having a second end including a handle control, each handle control coupled to the cross bar, the handle control of the first and second hoses including a releasably coupled J-shaped canula extending therefrom, the handle control of the third hose including a releasably coupled funnel-shaped saliva receptacle extending therefrom;

C) the interior of the outer casing is divided into upper, lower, and central levels by first and second divider walls, the upper level positioned beneath the lid and adapted to permit storage of various items therein, the central level is divided into a plurality of compartments including a motorized suction device and backup battery, the motorized suction device including a planar circular helix coupled to a rotating motor, an aperture positioned through the first divider wall below the helix, in the operative orientation the helix is rotated by the motor thereby drawing air from the central level and causing a low pressure area in the central level, the low pressure area causing suction of air flow from the second end of the hoses through their respective first ends, an electrical control box operatively couple to electrical outlets, a backup battery, a motorized suction device, and each handle control thereby permitting a handle to activate the suction device;

D) the lower level including a plurality of upwardly extending cushion springs, a collecting basin having a bottom and an open top positioned upon the springs, a screen positioned over the basin and beneath the first end of the hoses to filter debris passing therethrough, a mercury absorbing device positioned at the bottom of the basin;

E) a limit switch with an upper arm including a rubber stopper, a lower arm including a float, and a central member pivotally coupling the arms therebetween, the float positioned in the basin and rising as the fluid level in the basin rises thereby causing the rubber stopper to become tightly positioned within the aperture in the first divider wall causing cessation of suction through the hoses; and F) the handle control of each hose formed in a cylindrical configuration and including an upper surface and a lower surface, the lower surface formed as a grooved hand grip, the upper surface including a pivotally coupled depressible level biased by a resilient spring, each handle control including an aperture extending through its axis, the aperture including a sheet plug with a radial hole rotatably mounted therein, the plug rotatable to an open position permitting the passage of air and fluid therethrough, a rod operatively coupling the lever to the plug, a pair of electrical wires having a first end extending within the handle control, a bolt extending from the lever to a point adjacent the wires thereby electrically activating the apparatus and causing the rod to urge the plug into an open position.

2. A mobile multi-functional dental apparatus comprising:

A) a generally rectangular shaped outer casing having a front wall, a rear wall, sidewalls, a floor, an interior compartment, a hinged lid, a plurality of wheels and an electrical coupling device, the front wall including a plurality of switches and a lighted screen, a plurality of hoses each having a first end positioned through the outer casing and a second end including a handle control, each handle control including a device to permit activation and deactivation thereof; and B) the interior compartment divided into a plurality of levels by at least one divider wall, a first level including a motorized suction device, a second level positioned beneath the first level with an aperture extending through a divider wall separating the levels, the motorized suction device causing inward suction, a collecting basin for retaining fluid positioned within the second level, a limit switch including a stopper plug and a flotation device positioned within the basin, rising fluid level causing the flotation device to rise thereby forcing the stopper plug into the aperture causing cessation of suction through the hoses.

3. The mobile multi-functional dental apparatus as described in claim 2 wherein the handle control of each hose is formed in a cylindrical configuration and includes an upper surface and a lower surface, the lower surface formed as a grooved hand grip, each handle control including an aperture extending through its axis, each aperture having an outboard end, wherein the device, to permit activation and deactivation, comprises a depressible lever biased by a resilient spring and coupled to the upper surface of the handle control, the aperture including a sheet plug with a radial hole rotatably mounted therein, the plug rotatable to an open position permitting the passage of air and fluid therethrough, or a closed position preventing the passage of air and fluid therethrough, a rod operatively coupling the lever to the plug.

4. The mobile multi-functional dental apparatus as described in claim 3 and further including at least one J-shaped canula and at least one funnel-shaped saliva receptacle each adapted to be coupled to an outboard end of a handle control.

5. The mobile multi-functional dental apparatus as described in claim 3 wherein the interior compartment includes a hollow third level positioned above the first level beneath the hinged lid, the third level adapted to serve as a storage level.

6. The mobile multi-functional dental apparatus as described in claim 2 and further including a plurality of upwardly extending cushion springs positioned at a lowermost extent of the second level beneath the collecting basin, the cushion springs adapted to minimize vibration of the basin during movement of the apparatus.

* * * * *